(12) United States Patent
Razavi

(10) Patent No.: US 9,468,654 B1
(45) Date of Patent: Oct. 18, 2016

(54) DRUG DELIVERY COMPOSITIONS AND METHODS

(71) Applicant: WILKES UNIVERSITY, Wilkes-Barre, PA (US)

(72) Inventor: Ali Razavi, Dallas, PA (US)

(73) Assignee: Ali Razavi, Dallas, PA (US)

( * ) Notice: Subject to any disclaimer, the term of this patent is extended or adjusted under 35 U.S.C. 154(b) by 13 days.

(21) Appl. No.: 14/675,836

(22) Filed: Apr. 1, 2015

Related U.S. Application Data

(60) Provisional application No. 61/973,903, filed on Apr. 2, 2014.

(51) Int. Cl.
| | |
|---|---|
| *A61K 33/40* | (2006.01) |
| *A61K 31/198* | (2006.01) |
| *A61K 31/16* | (2006.01) |
| *A61P 17/02* | (2006.01) |
| *A61K 9/70* | (2006.01) |

(52) U.S. Cl.
CPC ............. *A61K 33/40* (2013.01); *A61K 9/7007* (2013.01); *A61K 31/16* (2013.01); *A61K 31/198* (2013.01)

(58) Field of Classification Search
None
See application file for complete search history.

(56) References Cited

U.S. PATENT DOCUMENTS

| | | | |
|---|---|---|---|
| 4,438,144 A | 3/1984 | Blackburn | |
| 5,436,228 A | 7/1995 | Postlethwaite et al. | |
| 5,736,165 A * | 4/1998 | Ripley | A61K 39/40 422/37 |
| 5,824,647 A | 10/1998 | Postlethwaite et al. | |
| 6,361,551 B1 * | 3/2002 | Torgerson | A61L 15/325 606/214 |
| 6,767,891 B2 | 7/2004 | Zaveri | |
| 7,160,553 B2 | 1/2007 | Gibbins et al. | |
| 8,679,523 B2 | 3/2014 | Gibbins et al. | |
| 2003/0091601 A1 | 5/2003 | Barbul | |
| 2010/0158818 A1 | 6/2010 | Jain et al. | |
| 2011/0229583 A1* | 9/2011 | Tran | A61K 33/40 424/613 |
| 2013/0157949 A1 | 6/2013 | Al-Mahmood et al. | |
| 2013/0288965 A1 | 10/2013 | Bolscher et al. | |
| 2013/0296530 A1 | 11/2013 | Bolscher et al. | |
| 2014/0120153 A1 | 5/2014 | Gibbons et al. | |

FOREIGN PATENT DOCUMENTS

| | | |
|---|---|---|
| WO | 2011157716 A1 | 12/2011 |
| WO | 2012060832 A1 | 5/2012 |

OTHER PUBLICATIONS

LoPachin et al., Molecular Mechanisms of Aldehyde Toxicity:A Chemical Perspective, Chemical Research in Toxicology (2014), vol. 27, pp. 1081-1091.*
Wu et al., Reactive Impurities in Excipients:Profling, Indentification and Mitigation of Drug-Excipient Incompatibility, AAPS PharmSciTech (2011), vol. 12, No. 4, pp. 1248-1263.*
Ramachandran et al., Kinetics and Mechanism of the Oxidation of Amino Acids by Peroxomonosulphate. Part 1., J. Chem. Soc. Perkin Trans. II (1984), pp. 1341-1344.*
Dvorak, Disinfection 101, Center for Food Security and Public Health (2008), pp. 1-20.*
Kannan et al., Studies on the Autocatalyzed Oxidation of Amino Acids by Peroxomonosulfate, Int. J. Chem. Kinet. (2003), vol. 35, pp. 475-483.*
Ecocid (R) S Technical Presentation (2009).*
"The Ultimate Formula for Advanced Wound Care," Nutrica Advanced Medical Nutrition, dated Sep. 2011, 4 pgs.
"Infection Reistant Coating," SPI-ARGENT™, undated, obtained Oct. 2014, 2 pgs.
O. Ermer and C. Robke, Crystal Structure and Chemical Stabilization of the Triple Salt (KHSO5)2 (KHSO4)(K2SO4), Institut for Organische Chemie der Univsrsitat, pp. 2908-2913.
Kimberly-Clark Health Care/OxyGenesys, pp. 1-4, Oct. 13, 2014, http://www.kchealthcare.com/products/surgical-solutions/oxygenesys.aspx.
N. Variankaval et al., "From Form to Function: Crystallization of Active Pharmaceutical Ingredients," AIChE Journal, Jul. 2008, vol. 54, No. 7, pp. 1682-1688.
A.E. Golovinsky, "RP-HPLC Analysis of Amino Acids With UV-Detection," Bulgarian Academy of Sciences, Provided by the NASA Astrophysics Data System, vol. 56, No. 12, 2003, pp. 75-78.
G. Maggio, et al., "A new protocol for the treatment of the chronic venous ulcers of the lower limb," PubMed Mobile-NCBI, pp. 1-2, May 2011, http://www.ncbi.nlm.nih.gov/m/pubmed/21559987/.
Dupont, Material Safety Data Sheet, "Oxone® Monopersulfate compound", Version 2.0, Revision Date May 11, 2011, Ref. 130000000134, pp. 1-8.
Sigma-Aldrich, Safety Data Sheet, "Potassium monopersulfate triple salt", Version 3.10, Revision Date Jul. 1, 2014, pp. 1-8.

* cited by examiner

*Primary Examiner* — Abigail Fisher
*Assistant Examiner* — Frank Choi

(57) ABSTRACT

A drug delivery composition is disclosed which includes a triple salt proxy functional group and at least one amino acid functional group. A method of forming the drug delivery composition includes reacting a triple salt with at least one amino acid in an aqueous environment. A biodegradable fabric is disclosed which includes a polymerized structure of a triple salt proxy functional group and at least one amino acid functional group.

13 Claims, 3 Drawing Sheets

DRUG DELIVERY COMPOSITIONS AND METHODS

CROSS-REFERENCE TO RELATED APPLICATIONS

This application claims the benefit of U.S. Provisional Patent Application No. 61/973,903, filed Apr. 2, 2014, entitled "Drug Delivery Compositions and Methods," the disclosures of which are incorporated by reference in its entirety and made part of the present U.S. utility patent application for all purposes.

FIELD OF THE INVENTION

This application is directed to drug delivery compositions and to methods for making and using the same, and more particularly to drug delivery compositions for wound treatment and to methods for making and using the same.

BACKGROUND OF THE INVENTION

The healing of a wound is a process that goes through a series of stages with varying cell types and chemical mediators in an appropriately moist environment. During this process, a wound site that is too moist or too dry may lead to inadequate cell proliferation. Traditional bandages have been used in an effort to retain appropriate levels of moisture but are inadequate in many cases for a variety of reasons.

Additionally, bacteria are a significant concern during wound healing, as uncontrolled populations of bacteria, which naturally contaminate all wounds, may give rise to an infection with potentially catastrophic consequences. This problem is complicated by the variety of bacteria which may be present, the increasing occurrence of drug-resistant bacteria, and patient drug allergies. While bandages again have been used to keep additional contamination from reaching the wound, they are again largely ineffective in many cases and further have little or no impact on contamination existing prior to bandage application.

Oxidative bursts in certain cells, such as macrophages of the vertebrate immune system, naturally produce a variety of highly reactive oxygenated species which can control bacterial populations. However, the amount of naturally occurring oxidative bursts is sometimes inadequate to quickly resolve contamination. This leads to greater possibility of infection, particularly where environments having lesser or greater moisture undesirably result in slower healing.

Accordingly, it would be desirable to provide and deliver multifunctional compounds with a broad spectrum of wound healing properties to a wound site that overcomes some or all of these and other drawbacks that currently exist in wound healing.

BRIEF DESCRIPTION OF THE INVENTION

In one exemplary embodiment, a drug delivery composition includes a triple salt proxy functional group and at least one amino acid functional group.

In another exemplary embodiment, a method of forming a drug delivery composition includes reacting a triple salt with at least one amino acid in an aqueous environment.

In yet another exemplary embodiment, a biodegradable fabric includes a polymerized structure of a triple salt proxy functional group and at least one amino acid functional group.

BRIEF DESCRIPTION OF THE DRAWINGS

Wherever possible, the same reference numbers will be used throughout the drawings to represent the same parts.

DETAILED DESCRIPTION OF THE INVENTION

Figure 1A:
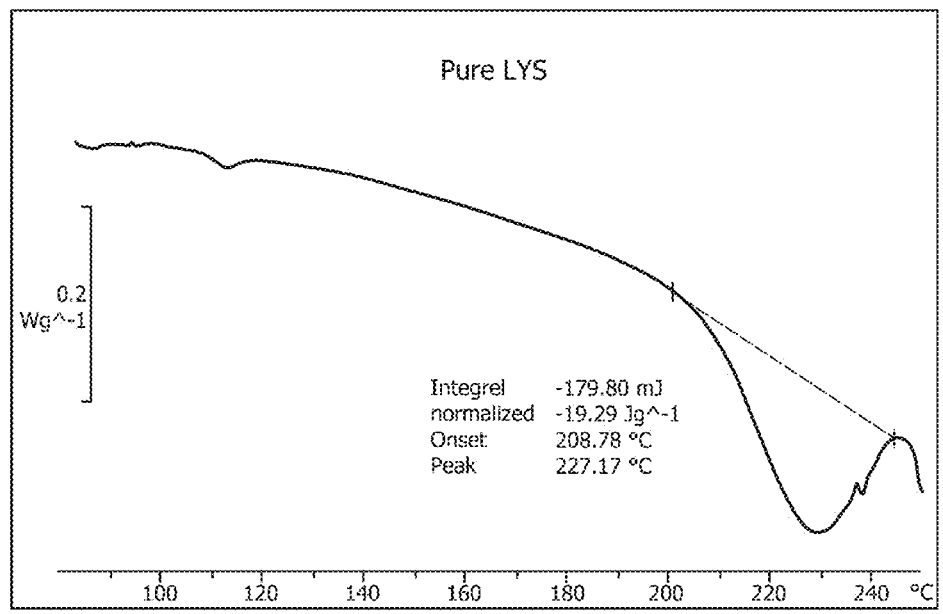
FIGS. 1A and B show thermographs comparing the melting of (1A) lysine and (1B) a lysine-based drug delivery composition, according to an embodiment of the disclosure.
Figure 1B:
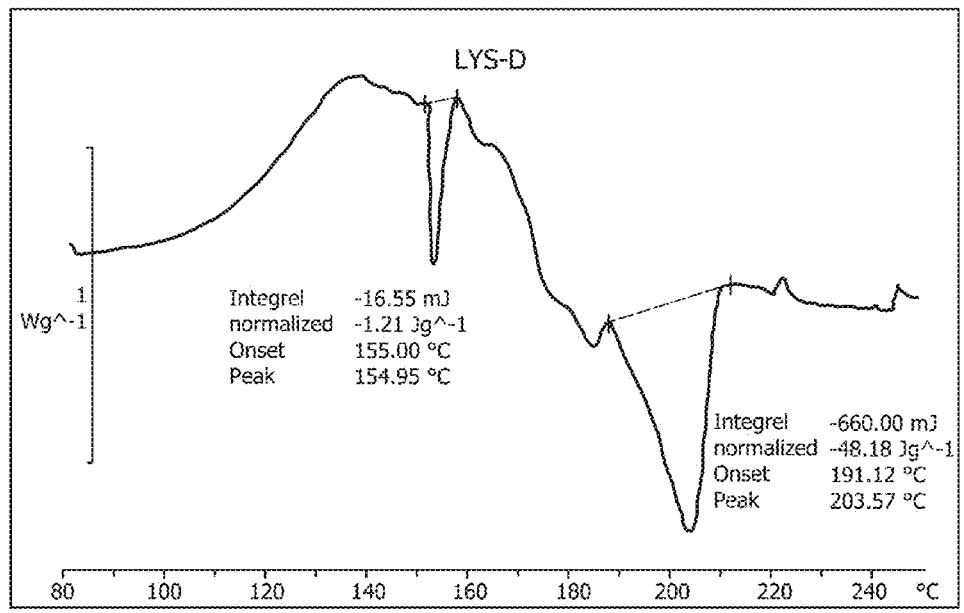

The drug delivery compositions disclosed herein are compounds that simultaneously provide the health benefits of an amino acid as well as antimicrobial properties approximating the qualities of stable peroxides produced by oxidative bursts. The drug delivery compositions include a triple salt proxy functional group and at least one amino acid functional group.

The at least one amino acid functional group of the compound includes amino acid health benefits. Amino acids are necessary for the synthesis of proteins, to provide nitrogen-bases energy for mitochondria for cell proliferation, to stop or reduce inflammation, to replace or repair damaged cells and to help cells synthesize extracellular matrix and collagen. Also, amino acids contribute to wound angiogenesis, which may be initiated by the early release of growth factors, such as fibroblast growth factor-2 (FGF-2) and vascular endothelial growth factors (VEGF) for wound healing processes. As used herein "amino acid health benefits" encompass health-related properties such as, but not limited to, stopping or reducing inflammation of the wound, replacing or repairing damaged cells at the wound, stimulating cells to synthesize extracellular matrix, stimulating cells to synthesize collagen, and combinations thereof.

Amino acids which may be employed in the compounds of exemplary embodiments include, but are not limited to, glutamine, alanine, aspartic acid, lysine, glycine, cysteine, arginine, proline, and combinations thereof. As used herein, "amino acid functional group" refers to the derivative form of an amino acid resulting from the reaction of the amino acid with a triple salt. Without being bound by theory, it is believed that the amino acid functional group may be a protonated amino acid. In one embodiment, the drug delivery composition includes a plurality of amino acid functional groups.

Triple salts disassociate highly reactive oxygenated species when exposed to an environment with elevated moisture levels and may approximate the effects of naturally occurring oxidative bursts. Triple salts possess only limited antimicrobial efficacy, due in part to the very slow rate of solid to liquid transformation of triple salts when exposed to elevated moisture levels. Further, triple salts have limited shelf life and contain hazardous impurities, including, but not limited to, irritants. In exemplary embodiments, these limitations of neat triple salts are overcome while the benefits are retained by compounding a triple salt proxy functional group with at least one amino acid functional group.

The triple salt proxy functional group is a highly reactive oxygenated species capable of killing bacteria, fungi, and viruses with a high kill rate. The triple salt proxy functional group may also provide intracellular chemical energy transfer for cellular metabolism. In particular, the triple salt proxy functional group may stimulate cellular respiration. The triple salt proxy functional group may also stimulate the physiological process through which new blood vessels are formed from pre-existing vessels. Further, the triple salt proxy functional group may increase collagen deposition in the wound by increasing oxygenation of the wound.

In one embodiment, the triple salt proxy functional group exhibits broad spectrum antimicrobial activity against bacteria, fungi, viruses, or combinations thereof, including, but not limited to, killing *Staphylococcus Aureus* (MRSA), *Salmonella typhimurium, Pseudomonas aeruginosa, Klebsiella pneumonia, Escherichia coli, Enterococcus, Enterobacter cloacae, Corynebacterium, pseudodiptherium, Corynebacterium pseudodiptherium, Candida albicans*, and Hepatitis A virus (HAv).

Any triple salt or peroxide, including, but not limited to, sodium, magnesium and calcium peroxides with peroxy active chemistry which are biologically safe for mammals may be used to provide the triple salt proxy functional group of the compound in accordance with exemplary embodiments. Suitable triple salts include, but are not limited to, potassium peroxymonosulfate, which has the stoichiometry $(K^+HSO_5^-)_2(KHSO_4^-)(K_2^+SO_4^{2-})$, and which results in the triple salt proxy functional group of $K+HSO_5^-$.

The compound in accordance with exemplary embodiments may be formulated through a variety of mechanisms, typically via wet chemistry synthesis. In one embodiment, at least one amino acid is mixed with the triple salt, followed by reaction in an aqueous environment to preferentially dissolve the triple salt, which immediately interacts with the at least one amino acid to form a slurry. In another embodiment, the triple salt may be dissolved in an aqueous environment first, followed by subsequent addition of the at least one amino acid to form the compound in a liquid slurry. The triple salt may be reacted with a plurality of amino acids in the aqueous environment.

Without being bound by theory, Fourier Transform Infrared (FTIR) spectroscopy of exemplary embodiments of drug delivery compositions prepared according to the present disclosure including varying weight percents of amino acids, suggests that triple salt proxy functional groups may be incorporated into amino acid crystal structures at amino acid weight percent content of the drug delivery compositions equal to about the solubility limit of the particular amino acid employed in the drug processing. Above the solubility limit by weight of the amino acid inclusion, by wet chemistry processing, the structure of the drug delivery composition transitions to a polymerized structure having rubber-like characteristics, which is distinguishable from the crystalline structure of the drug delivery compositions.

The resulting compound may be stored in any suitable form, including, but not limited to, a liquid, freeze-dried, filtered and dried for storage as a powder base material, or incorporated into a medical foam. In one embodiment, the powder base material includes the property of rapid solubility in an aqueous solution. The compound is stable for long periods of time without significant reduction in the antimicrobial properties stemming from the triple salt proxy functional group or the healing properties stemming from the at least one amino acid functional group. In one embodiment, the drug delivery composition loses less than 0.1% of its antimicrobial activity per month when stored in a hermetically sealed enclosure.

Without being bound by theory, it is believed that uniform dispersion of the amino acids in the drug delivery composition is critical for delivering consistent health benefits. Therefore, it is believed that agglomeration of the amino acids in the drug delivery composition should be avoided.

The drug delivery composition may, depending upon the form selected, be incorporated into any suitable medical product. Exemplary products include, but are not limited to, disposable nonwoven medical fabrics, biodegradable wound dressings, foam wound dressings, composite wound dressings, surgical pads, post-operative dressings, nasal packing for ENT applications, and face masks.

In one embodiment, a biodegradable fabric includes the polymerized structure of a triple salt proxy functional group and at least one amino acid functional group having rubber-like characteristics. In another embodiment, a powder base form of the drug delivery composition is incorporated within a fiber by powder or solution blending and extrusion to fiber form. In an alternate embodiment, fibers are formed by electrospinning a solution including the drug delivery composition. Fibers including the drug delivery composition may include surfaces which are the active site to deliver the drug delivery composition for healing purposes.

Top coating synthetic or natural fabrics with the drug delivery composition may form a drug delivery layer which is biodegradable and which may be consumed during the duration of a healing process. In one embodiment, the drug delivery layer is applied to any suitable fabric, including, but not limited to, hyaluronic acid-based fabric, including, but not limited to, non-woven fabric and scaffold fabric, non-woven fabric, polyurethane foam fabric, polyolefin fabric, cotton-based fabric, semi-permeable fabric, silicone-based fabric, foam fabric, alginate fabric, hydrogel fabric, hydrocolloid fabric, capillary action fabric, hydrofiber fabric, carbon/charcoal-enriched fabric, honey enriched fabric, silver impregnated fabric, biodegradable fabric, wound dressing fabric in single or multilayered composite forms, any other fabrics that are currently being used for wound dressing, and combinations thereof. The drug delivery layer may be applied to cover continuously the entire surface of a fabric or may be applied in a specific pattern designed to optimize delivery of the drug delivery compound for healing purposes. In one embodiment, the drug delivery composition is applied to a fabric as a solution and then freeze dried to an embedded powder form.

In a further embodiment, the triple salt proxy functional group of the polymerized structure is $K^+HSO_5^-$, or any suitable triple salt proxy functional group. In another embodiment, the amino acid functional group of the polymerized structure is selected from the group consisting of derivatives of glutamine, alanine, aspartic acid, lysine, glycine, cysteine, arginine, proline, and combinations thereof. The biodegradable fabric including the polymerized structure may include the property of broad spectrum antimicrobial activities against bacteria, fungi and viruses, the property of amino acid health benefits, or both.

Foam applications are preferred in many cases, as current medical foam products may be constructed with varying absorptive properties that may be adapted to heavily, moderately, or mildly exudative wounds to enable better moisture control, which may help enhance performance of the exemplary compounds.

The drug delivery composition may be utilized for any suitable purpose, including, but not limited to, diabetic wound healing, liquid and solid base disinfection with rapid kill rate and environmentally safe profile, anti-scar applications, nasal liquid and solid base dispensing delivery, and liquid base wound cleaning with multiple functionality. In one embodiment, a method of treating an individual having a wound includes introducing the drug delivery composition into the wound. The amount of drug delivery composition introduced into the wound may be any suitable and medically effective amount.

EXAMPLES

The principles of the invention are demonstrated with respect to the following examples, which are presented by way of exemplification only and not intended in any way to limit the more general teachings described herein.

Example 1

150 grams of potassium peroxymonosulfate triple salt were mixed with 5 g Lysine amino acid. This mixture was reacted with 100 g water in order to preferentially dissolve the $K^+HSO_5^-$ component out of the triple salt with immediate reaction with the amino acid, forming a slurry. This slurry was mechanically stirred in a glass beaker for a period of one hour. After one hour, the slurry mixture was vacuum filtered, and the resulting liquid material was collected and crystallized at room temperature. The crystallized powder materials were air dried to yield a dry powder base material. The powder base material was collected in a resealable plastic bag, and stored in a plastic bucket with anhydrous calcium sulfate desiccant material (Drierite®, W. A. Hammond Drierite Co. Ltd., Xenia, Ohio) placed in the bottom of the bucket. The bucket was closed with an air-tight lid. The activity of the triple salt proxy functional group decreased by less than 0.1% per month over the course of a year.

Figure 2:
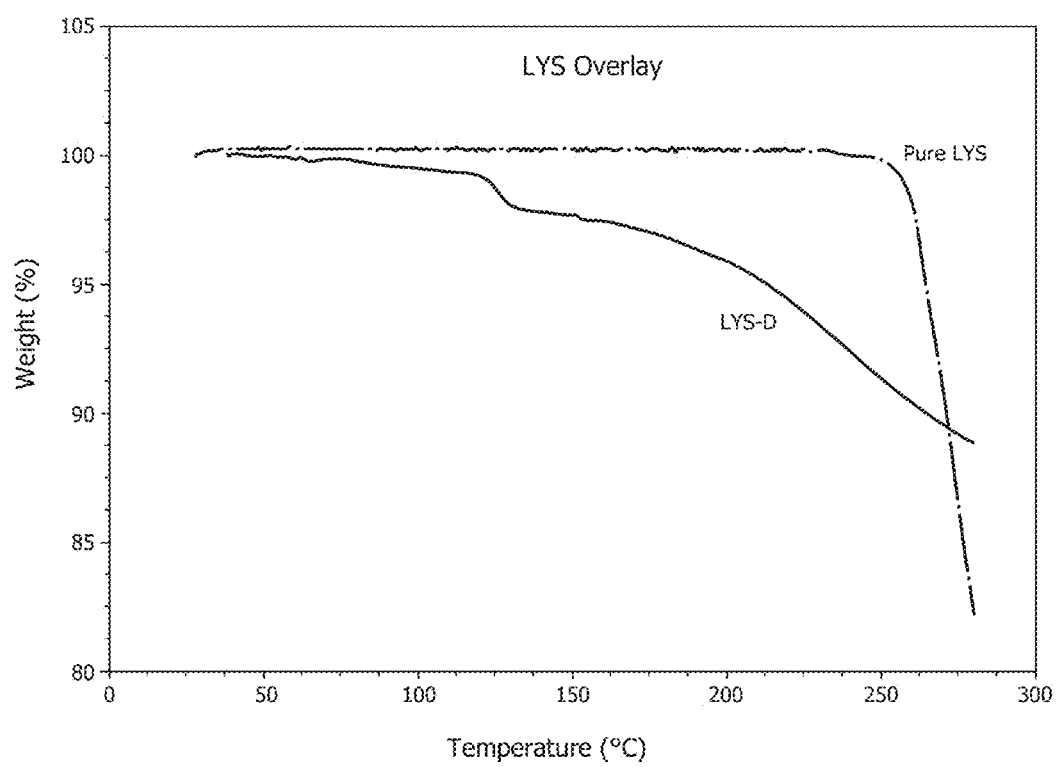
FIG. 2 shows thermographs comparing the thermal stability of (a) lysine and (b) a lysine-based drug delivery composition, according to an embodiment of the disclosure.

Referring to FIGS. 1A and B, differential scanning calorimetry thermographs compare the melting of (1A) lysine and (1B) a lysine-based drug delivery composition, according to this example. The thermographs demonstrate the melting point of the lysine-based drug delivery composition is about 191° C., as compared to lysine which has a melting point of 209° C. Referring to FIG. 2, thermal gravimetric analysis thermographs show that the thermal stability of the lysine-based drug delivery composition (onset decomposition temperature of about 200° C.) is significantly lower than the thermal stability of lysine (onset decomposition temperature of about 257° C.). These observations, further confirmed with Raman spectroscopy and x-ray powder diffraction, are consistent with the nanosizing effect on melting point and thermal stability of crystals due to the increased surface to volume ratio. This suggests that the lysine in the lysine-based drug delivery composition, according to this embodiment, is nano-sized and uniformly distributed, and therefore not subject to significant agglomeration of the amino acid.

Example 2

150 grams of potassium peroxymonosulfate triple salt were mixed with 5 g Glutamine amino acid. This mixture was reacted with 100 g water in order to preferentially dissolve the $K^+HSO_5^-$ component out of the triple salt with immediate reaction with the amino acid, forming a slurry. This slurry was mechanically stirred in a glass beaker for a period of one hour. After one hour, the slurry mixture was vacuum filtered, and the resulting liquid material was collected and freeze dried to yield a powder base material. The powder base material was collected in a resealable plastic bag, and stored in a plastic bucket with anhydrous calcium sulfate desiccant material (Drierite®, W. A. Hammond Drierite Co. Ltd., Xenia, Ohio) placed in the bottom of the bucket. The bucket was closed with an air-tight lid. The activity of the triple salt proxy functional group decreased by less than 0.1% per month over the course of a year.

Figure 3A:
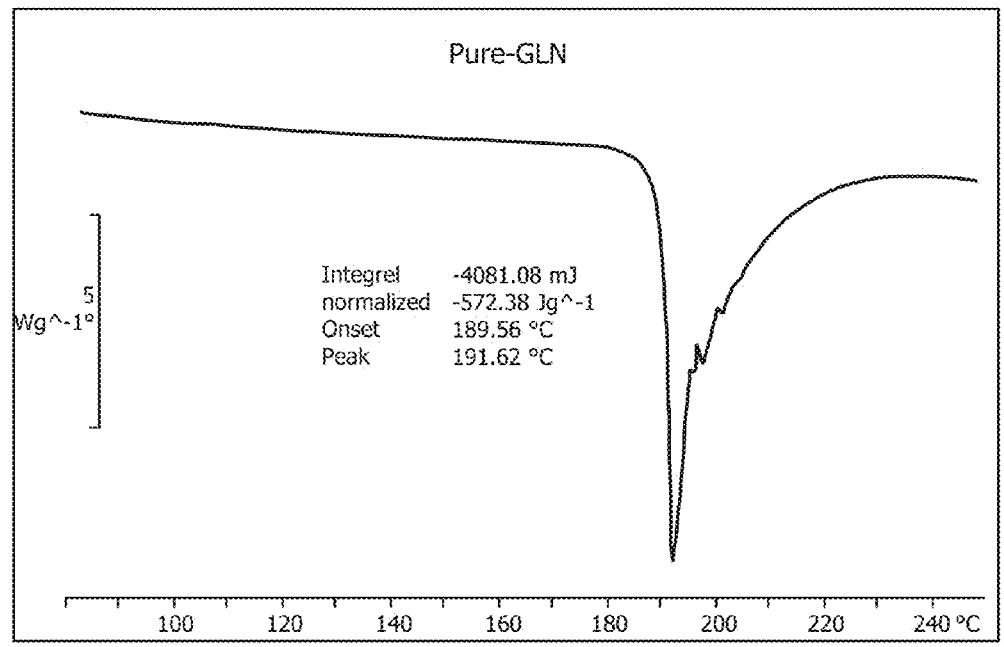
FIGS. 3A and B show thermographs comparing the melting of (3A) glutamine and (3B) a glutamine-based drug delivery composition, according to an embodiment of the disclosure.
Figure 3B:
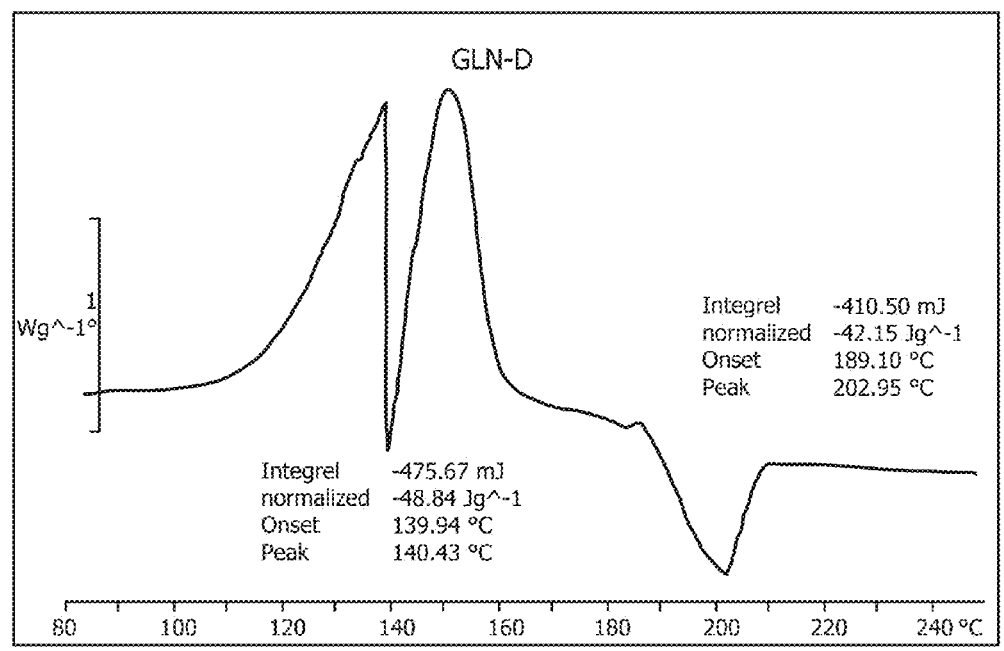

Referring to FIGS. 3A and B, differential scanning calorimetric thermographs compare the melting of (3A) glutamine and (3B) a glutamine-based drug delivery composition, according to this example. The thermographs demonstrate the melting point of the glutamine-based drug delivery composition is about 189° C. as compared to glutamine which has a melting point of 190° C. These observations, further confirmed with Raman spectroscopy and x-ray powder diffraction, are consistent with the nanosizing effect on melting point and thermal stability of crystals due to the increased surface to volume ratio. This suggests that the glutamine in the glutamine-based drug delivery composition, according to this embodiment, is nano-sized and uniformly distributed, and therefore not subject to significant agglomeration of the amino acid.

Example 3

150 grams of peroxymonosulfate triple salt were reacted with 100 g water in order to preferentially dissolve the $K^+HSO_5$ component out of the triple salt, forming a slurry. This slurry was mechanically stirred in a glass beaker for a period of one hour. After one hour, the slurry mixture was vacuum filtered, and the resulting liquid was reacted with 5 g Glycine amino acid. The reaction product was collected and freeze dried to yield a powder base material. The powder base material was collected in a resealable plastic bag, and stored in a plastic bucket with anhydrous calcium sulfate desiccant material (Drierite®, W. A. Hammond Drierite Co. Ltd., Xenia, Ohio) placed in the bottom of the bucket. The bucket was closed with an air-tight lid. The activity of the triple salt proxy functional group decreased by less than 0.01% per month over the course of a year.

Example 4

44 grams of peroxymonosulfate triple salt were reacted with 100 g water in order to preferentially dissolve the $K^+HSO_5^-$ component out of the triple salt, forming a slurry. This slurry was mechanically stirred in a glass beaker for a period of one hour. After one hour, the slurry mixture was vacuum filtered, and the resulting liquid was reacted with 5 g Glycine amino acid. The reaction product was collected and freeze dried to yield a powder base material. The powder base material was collected in a resealable plastic bag, and stored in a plastic bucket with anhydrous calcium sulfate desiccant material (Drierite®, W. A. Hammond Drierite Co. Ltd., Xenia. Ohio) placed in the bottom of the bucket. The bucket was closed with an air-tight lid. The activity of the triple salt proxy functional group decreased by less than 0.1% per month over the course of a year.

Antimicrobial activity for the drug delivery compositions of Examples 1 and 3 was measured with standard Kirby-Bauer antibiotic testing for *Staphylococcus aureus* (MRSA) and *Pseudomonas aeruginosa*.

Kirby-Bauer antibiotic testing (KB testing or disk diffusion antibiotic sensitivity testing) is a test which uses antibiotic-impregnated wafers to test whether particular bacteria are susceptible to specific antibiotics. A known quantity of bacteria is grown on agar plates in the presence of thin wafers or powder base materials containing relevant antibiotics. If the bacteria are susceptible to a particular antibiotic, an area of clearing surrounds the wafer where bacteria are not capable of growing (called a zone of inhibition).

The bacteria in question are swabbed uniformly across a culture plate. Five milligrams of powder base materials are then placed on the surface of the agar. The compound diffuses from the powder into the agar. The concentration of the compound will be highest next to the disk, and will decrease as distance from the disk increases. If the compound is effective against bacteria at a certain concentration, no colonies will grow where the concentration in the agar is greater than or equal to the effective concentration. This is the zone of inhibition. This, along with the rate of antibiotic diffusion, is used to estimate the bacteria's sensitivity to that particular antibiotic. In general, larger zones correlate with smaller minimum inhibitory concentration (MIC) of antibiotic for that bacterium. Inhibition produced by the test is compared with that produced by known concentration of a reference compound.

There were no solid powder materials left on the plates due to rapid conversion of the solid powder bases to liquids for both Examples 1 and 3 upon exposure to the moist environments on the plates.

Cytotoxicity of the drug delivery composition was tested using human coronary arterial smooth muscle cells grown in a sterile, liquid basal medium for the culture of human smooth muscle cells (Medium 231 available from Life Technologies) supplemented with smooth muscle growth supplement until the cells became confluent. After reaching confluence, the cells were trypsinized and seeded at equal density in culture dishes and allowed to reach approximately 70% confluence.

Control dishes were fed with growth media, and treated cells were fed with growth media supplemented by ATCC 4330 4 mg/mL, ATCC 4330 8 mg/mL, GLN 1 mg/mL, or GLN 2.5 mg/mL, respectively. After two hours, cells were observed and a cell count was performed using trypan blue exclusion dye. Cells appeared healthy in all conditions and cell counts did not differ significantly, indicating that the drug delivery composition is not cytotoxic.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising a triple salt proxy functional group and at least one amino acid functional group, wherein the triple salt proxy functional group is $K^+HSO_5^-$.

2. The composition of claim 1, wherein the amino acid functional group is selected from the group consisting of derivatives of glutamine, alanine, aspartic acid, lysine, glycine, cysteine, arginine, proline, and combinations thereof.

3. The composition of claim 1, wherein the triple salt proxy functional group includes the property of broad spectrum antimicrobial activities against bacteria, fungi and viruses.

4. The composition of claim 1, wherein the composition further comprises a plurality of amino acid functional groups.

5. The composition of claim 4, wherein the plurality of amino acid functional groups further comprises amino acid health benefits.

6. The composition of claim 1, wherein the composition is a powder base material.

7. The composition of claim 6, wherein the powder base material further comprises the property of rapid solubility in an aqueous solution.

8. A method for treating a wound comprising applying the composition of claim 1 to the wound.

9. A method for forming a composition comprising reacting a triple salt with at least one amino acid in an aqueous environment, wherein the triple salt is potassium peroxymonosulfate, and wherein the composition includes a triple salt proxy functional group and at least one amino acid functional group.

10. The method of claim 9, wherein the at least one amino acid is selected from the group consisting of glutamine, alanine, aspartic acid, lysine, glycine, cysteine, arginine, proline, and combinations thereof.

11. The method of claim 9 further comprising reacting the triple salt with a plurality of amino acids in the aqueous environment.

12. The method of claim 9, wherein the triple salt proxy functional group further comprises the property of broad spectrum antimicrobial activities against bacteria, fungi and viruses.

13. The method of claim 9, wherein the composition further comprises amino acid health benefits.

* * * * *